United States Patent [19]

Nofre et al.

[11] Patent Number: 4,673,582

[45] Date of Patent: Jun. 16, 1987

[54] NOVEL SWEETENING AGENTS, PROCESS FOR SWEETENING VARIOUS PRODUCTS AND COMPOSITIONS CONTAINING SUCH SWEETENING AGENTS

[75] Inventors: Claude Nofre, Lyons; Jean M. Tinti, Meyzieu, both of France

[73] Assignee: Universite Claude Bernard/Lyon 1, Lyons, France

[21] Appl. No.: 836,383

[22] Filed: Mar. 5, 1986

[30] Foreign Application Priority Data

Mar. 19, 1985 [FR] France ................... 85 04241

[51] Int. Cl.$^4$ .............................. A23L 1/26
[52] U.S. Cl. ................... 426/548; 558/413; 558/414; 560/13; 560/16; 560/34; 562/439; 562/430; 562/426; 562/437; 514/974; 424/48; 424/49; 424/64; 131/276; 131/279
[58] Field of Search ............. 558/413, 414; 560/34, 560/13, 16; 562/439, 430, 437, 426; 514/974; 424/48, 49, 64; 426/548; 564/109; 131/276, 279; 260/990.2

[56] References Cited

U.S. PATENT DOCUMENTS

| | | | |
|---|---|---|---|
| 3,492,131 | 1/1970 | Schlatter | 562/450 |
| 3,642,491 | 2/1972 | Schlatter | 560/41 |
| 3,714,139 | 1/1973 | Schlatter | 560/125 |
| 3,800,046 | 3/1974 | Schlatter | 560/41 |
| 4,426,521 | 1/1984 | Tanaka et al. | 564/108 |

FOREIGN PATENT DOCUMENTS

| | | | |
|---|---|---|---|
| 1027113 | 2/1978 | Canada | 562/443 |
| 0048051 | 1/1981 | European Pat. Off. | 562/443 |
| 2533210 | 3/1984 | France | 426/548 |

OTHER PUBLICATIONS

Ariyashi et al., Bulletin of the Chemical Society of Japan, 47(2), 326-330 (1974).

J. M. Tinti et al., Naturwissenchaften, 68, 143-145 (1981).

J. M. Tinti et al., Naturwissenchaften, 67, 192-194 (1980).

J. W. Tsang, J. Med. Chem, 27, 1663-1668 (1984).

*Primary Examiner*—James H. Reamer
*Attorney, Agent, or Firm*—Parkhurst & Oliff

[57] ABSTRACT

Sweetening agents of general formula:

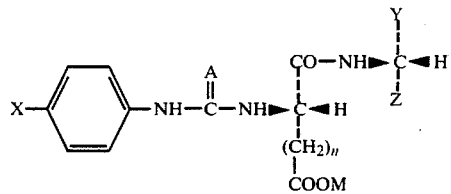

wherein:

X is a CN, COOC$_1$-C$_3$ alkyl, COC$_1$-C$_3$ alkyl, CONH-C$_1$-C$_3$ alkyl, SO$_2$C$_1$-C$_3$ alkyl, SOC$_1$-C$_3$ alkyl, SO$_2$NHC$_1$-C$_3$ alkyl, NO$_2$, F, Cl substituent;

n is a number equal to 0 or 1;

M is a hydrogen atom, or an organic or inorganic physiologically acceptable cation;

Y is a COOC$_1$-C$_3$ alkyl, C$_1$-C$_3$ alkyl, CH$_2$OH, CHOHCH$_3$, CF$_3$ substituent;

Z is a C$_1$-C$_5$ n-alkyl, isobutyl, isopentyl, phenyl, cyclohexyl, benzyl, cyclohexylmethyl, CH$_2$C$_6$H$_4$OH(p), CH$_2$OC$_1$-C$_4$ alkyl, CH$_2$COOC$_1$-C$_4$ alkyl, CH$_2$SC$_1$-C$_4$ alkyl, CH$_2$CH$_2$SCH$_3$, CH$_2$CH$_2$SO$_2$CH$_3$, COOC$_1$-C$_4$ alkyl, COOC$_3$-C$_7$ cycloalkyl, CONH-C$_2$-C$_4$ alkyl, CONHC$_3$-C$_7$ cycloalkyl, CONHC$_3$-C$_7$ thiacycloalkyl, or CONHCH$_2$COOCH$_3$ group;

characterized in that A is an N—CN group.

10 Claims, No Drawings

NOVEL SWEETENING AGENTS, PROCESS FOR SWEETENING VARIOUS PRODUCTS AND COMPOSITIONS CONTAINING SUCH SWEETENING AGENTS

The invention relates to novel sweetening agents. It further relates to their use for sweetening different products and to compositions containing such sweetening agents.

Applicant's European Patent Application No. EP-A-0 107 597 (U.S. patent application Ser. No. 532,499) describes as novel chemical compounds and sweetening agents, compounds having the following general formula:

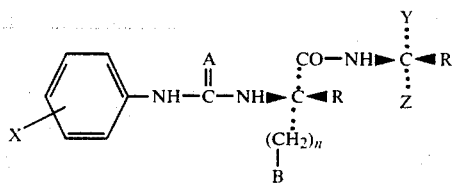

in which A is an atom of sulphur or oxygen, or an imino or methylene group.

It has since been found that said compounds, when their radical A is a sulphur atom, are insufficiently stable for certain uses as sweetening agents, such as for example with drinks; there indeed occurs, when in solution, a slow hydrolysis of the thiocarbonyl groups of these compounds. It has also been found that said compounds, when their radical A is an imino group, are not very soluble in water, this being a disadvantage if they are used as sweetening agents; in addition, said compounds have a limited sweetening power, this resulting in an increase of their cost price.

It is the object of the present invention to overcome the aforesaid drawbacks by proposing a sweetening agent of the formula:

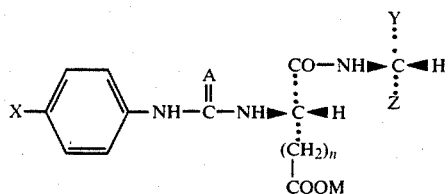

Wherein:
X is a CN, $COOC_1$-$C_3$ alkyl, $COC_1$-$C_3$ alkyl, $CONH$-$C_1$-$C_3$ alkyl, $SO_2C_1$-$C_3$ alkyl, $SOC_1$-$C_3$ alkyl, $SO_2NHC_1$-$C_3$ alkyl, $NO_2$, F, Cl substituent;
n is a number equal to 0 or 1;
M is a hydrogen atom, or an organic or inorganic physiologically acceptable cation;
Y is a $COOC_1$-$C_3$ alkyl, $C_1$-$C_3$ alkyl, $CH_2OH$, $CHOHCH_3$, $CF_3$ substituent;
Z is a $C_1$-$C_5$ n-alkyl, isobutyl, isopentyl, phenyl, cyclohexyl, benzyl, cyclohexylmethyl, $CH_2C_6H_4OH(p)$, $CH_2OC_1$-$C_4$ alkyl, $CH_2COOC_1$-$C_4$ alkyl, $CH_2SC_1$-$C_4$ alkyl, $CH_2CH_2SCH_3$, $CH_2CH_2SO_2CH_3$, $COOC_1$-$C_4$ alkyl, $COOC_3$-$C_7$-cycloalkyl, $CONH$-$C_2$-$C_4$ alkyl, $CONHC_3$-$C_7$ cycloalkyl, $CONHC_3$-$C_7$ thiacycloalkyl, or $CONHCH_2COOCH_3$ group.

The sweetening agents according to the invention are characterized in that A is a N—CN group.

In other words, the invention differs from the solution proposed in the aforecited document in the special choice of the radical A, namely the N—CN group. This substitution is all the more novel and unexpected as it has never been heretofore proposed to use such a N—CN radical to obtain sweetening properties and it is known that this radical is in no way equivalent to the radicals proposed until now. Moreover, it is also known that a slight modification can entail an alteration of the nature and properties of a compound, especially as the relations between the substituents and the sweetening activity are totally unforeseeable (M. G. J. BEETS: Structure-Activity Relationships in Human Chemoreception, Applied Science Publ., London, 1978, p. 259-362).

Advantageously, in the sweetening agents according to the invention:

X is CN, $COOCH_3$, $COOC_2H_5$, $COCH_3$, $CONHCH_3$, $SO_2CH_3$, $SO_2NHCH_3$;

n is equal to 1;

M is a hydrogen atom or a $Na^+$, $K^+$, $NH_4^+$, $\frac{1}{2} Ca^{2+}$, $\frac{1}{2} Mg^{2+}$ cation;

Y is $COOCH_3$, $CH_3$, $CH_2OH$;

Z is a butyl, pentyl, isobutyl, isopentyl, phenyl, cyclohexyl, benzyl, cyclohexylmethyl, propylamide, 2-butylamide, dicyclopropylcarbinylamide, 2,2,4,4-tetramethylthietan-3-ylamide group.

Preferred sweetening agents according to the invention essentially are:

the N-[cyanoimino(4-X-phenylamino)methyl]-L-aspartyl-L-phenylalanine methyl ester derivatives of the formula:

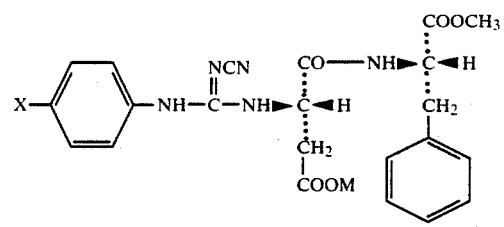

the N-[cyanoimino(4-X-phenylamino)methyl]-L-aspartic acid N-[(R)-α-methylbenzyl]α-monamide derivatives of the formula:

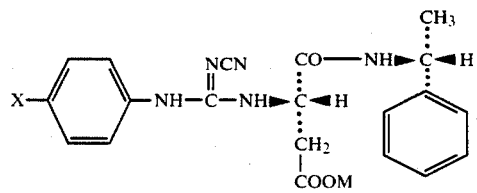

the N-[cyanoimino(4-X-phenylamino)methyl]-L-asparatyl-D-alanine N-(2-butyl)amide derivatives of the formula:

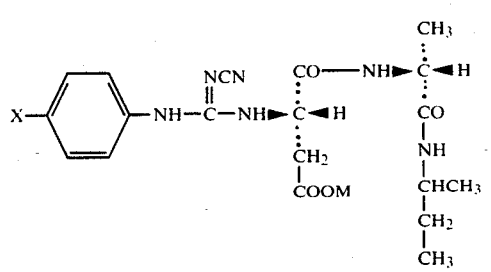

The compounds according to the invention can be prepared by condensation of the compound having the following general formulae:

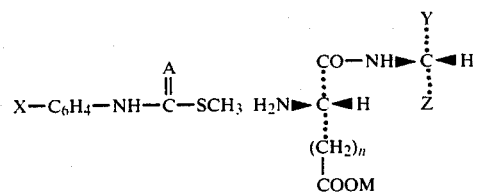

The reaction between the two compounds can be carried out in the presence of a base, said base being selected from the group including sodium hydroxide, potassium hydroxide, or a tertiary amine such as for example, triethylamine.

The condensation is carried out at boiling point in a mixture of water and ethanol.

The invention further relates to sweetening compositions containing such compounds, whether alone or mixed with other sweetening compounds, and this in sufficient proportions to be physiologically acceptable and efficient.

The invention will be more readily understood on reading the following examples of embodiment given by way of information and non-restrictively.

EXAMPLE 1

Synthesis of N-[cyanoimino(4-cyanophenylamino)-methyl]-L-aspartic acid N-[(R)-α-methylbenzyl]α-monoamide:

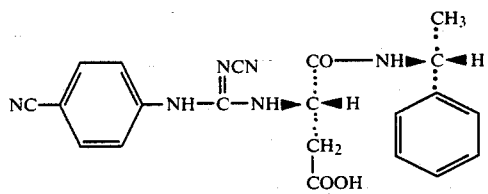

STEP 1

Preparation of N-(4-cyanophenyl)-N'-cyano-S-methylisothiourea:

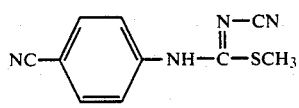

A mixture of 32 g (0.2 mole) of 4-cyanophenyl isothiocyanate and 12.8 g (0.2 mole) of monosodium cyanamide in 100 cm³ of absolute ethanol is kept at the boiling point for 2 hours. After cooling, the resulting precipitate is filtered and washed with 200 cm³ of absolute ethanol. The solid is then suspended in a solution of dimethyl sulfate (25 g, that is, 0.2 mole) in 500 cm³ of ethanol; the mixture is heated for 2 hours at the boiling temperature. The final precipitate is filtered, washed with 2×100 cm³ of water and with 2×100 cm³ of ethanol, then dried in vacuo. 32.8 g (yield 70%) of a white solid with a melting point of 220°–225° C. are obtained.

STEP 2

A mixture of 2.3 g (0.01 mole) of L-aspartic acid N-[(R)-α-methylbenzyl]α-monoamide, 3.2 g (0.013 mole) of the compound obtained above and 0.4 g of sodium hydroxide in 20 cm³ of ethanol is heated under reflux for 4 hours. After cooling, the solid remaining in suspension is eliminated by filtration and the resulting filtrate is concentrated to dryness in vacuo. The residue obtained in this way is dissolved in 120 cm³ of a 2% aqueous sodium carbonate solution, then washed with dichloromethane (3×100 cm³). The aqueous phase is then acidified with a 3N HCl solution until a pH of around 2 is obtained. The resulting white solid is filtered, washed with 2×5 cm³ of water, then dried in vacuo. After recrystallization in dichloromethane, 3.1 g (yield 70%) of a white solid are obtained, of melting point 162° C.

The sweetening power of this compound is approximately 3000 (three thousand) times that of sucrose on a molar basis, in relation to a 2% sucrose solution, 2000 (two thousand) times in relation to a 5% solution and 800 (eight hundred) times in relation to a 10% solution. The assessment was carried out under the same conditions as those described in detail in European Patent Application No. EP-A-O 107 597 (U.S. patent application Ser. No. 532,499), cited in the preamble.

EXAMPLE 2

Synthesis of N-[cyanoimino(4-cyanophenylamino)-methyl]-L-aspartyl-L-phenylalanine methyl ester:

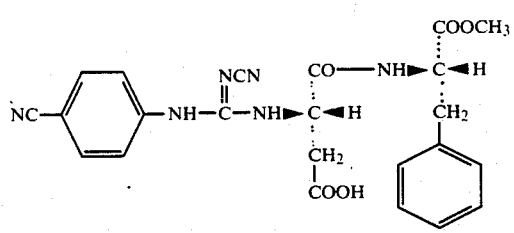

This compound, obtained according to a method identical to that of Example 1 (yield 20%; melting point 173° C., ethanol) has a very strong sweet taste. Its sweetening power is about 40,000 (forty thousand) times that of sucrose on a molar basis in relation to a 2% sucrose solution, 30,000 (thirty thousahnd) times in relation to a 5% solution and 10,000 (ten thousand) times in relation to a 10% solution.

EXAMPLE 3

Synthesis of N-[cyanoimino(4-methoxycarbonyl-phenylamino)methyl]-L-aspartic acid N-[(R)-α-methylbenzyl]α-monoamide:

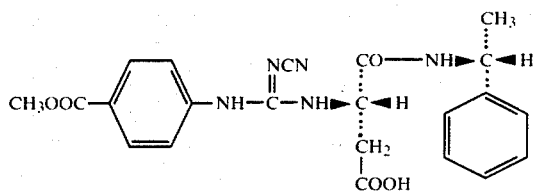

This compound, obtained according to a method identical to that of Example 1 (yield 60%; melting point 96° C.; amorphous) has a sweetening power which is about 1200 (one thousand two hundred) times that of sucrose on a molar basis in relation to a 2% sucrose solution, 800 (eight hundred) times in relation to a 5% solution, 400 (four hundred) times in relation to a 10% solution.

EXAMPLE 4

Synthesis of N-[cyanoimino(4-cyanophenylamino)-methyl]-L-aspartic acid N-(L-2-isoheptyl)α-monoamide:

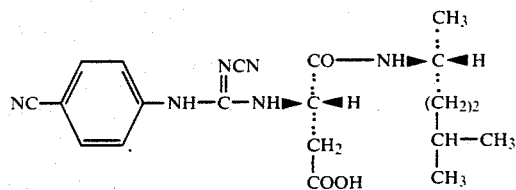

This compound, obtained according to a method identical to that of Example 1 (yield 45%; melting point 178°-180° C., ethanol) has a sweetening power which is approximately 4000 (four thousand) times that of sucrose on a molar basis in relation to a 2% sucrose solution, 2500 (two thousand five hundred) times in relation to a 5% solution, 1800 (one thousand eight hundred) times in relation to a 10% solution.

EXAMPLE 5

Synthesis of N-[cyanoimino(4-cyanophenylamino)-methyl]-L-aspartyl-D-alanine N-(2-butyl)amide:

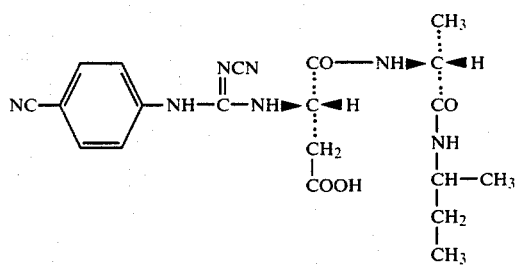

This compound, obtained according to a method identical to that of Example 1 (yield: 45%; melting point 187° C., amorphous) has a sweetening power which is about 800 (eight hundred) times that of sucrose on a molar basis in relation to a 2% solution of sucrose.

The sweetening agents according to the invention present many advantages over the products currently found on the market. Among these advantages:
strong sweetening power,
low cost,
excellent taste quality with no bitter after-taste.

Because these compounds are non-nutritive, non-fermentable and non-cariogenic, they can be successfully used, either alone or with other sweeteners, by being added in adequate quantity, to sweeten a large number of products, such as for example and non-restrictively:
as non-nutritive tabletop sweeteners (in tablets, packets, etc.),
in dietetic low-calorie products such as for example in beverages, concentrated drinks, instant drinks in powder form, and in pre-sweetened instant coffees, teas, chocolates, in dairy products (milks, yogurts, pre-sweetened powdered milks, whipped creams, etc.) or similar dairy products, in pre-sweetened breakfast cereals and drinks, in desserts (jellies, puddings and other cakes and pastries) and in frozen desserts, ice creams and whipped cream toppings, in bakery products, jams marmelade, dietetics, jellies and honeys, in dressings, ketchups, pickles, sauces and other food flavorings, in confectionery (candies, chewy candies, chocolate or cocoa confectionery, marshmallows, etc.)
in chewing gums,
in toothpastes and lipsticks,
in mouth-washes and gargles,
in various pharmaceutical, veterinary and cosmetic preparations (to improve the taste of the preparation or to conceal the unpleasant taste of certain products),
in various hygiene articles,
in tobaccos,
in animal foods, etc.

The sweetening agents according to the invention can be advantageously used mixed with a compatible carrier, such as for example and non-restrictively, starch, malto-dextrins, cellulose, methylcellulose, carboxymethylcellulose, sodium alginate, pectins, gums, lactose, maltose, glucose, leucine, glycerol, mannitol, sorbitol, and acids such as phosphoric, citric, tartaric, fumaric, benzoic, sorbic and propionic acids, their sodium, potassium and calcium salts, and sodium bicarbonate.

The sweetening agents according to the present invention can also be used in combination with other sweetening agents such as, for example, and non-restrictively, sucrose, corn syrups, fructose, aspartame, glycrrhizin, xylitol, acesulfame-K, thaumatin.

What is claimed is:

1. Sweetening agents of the general formula:

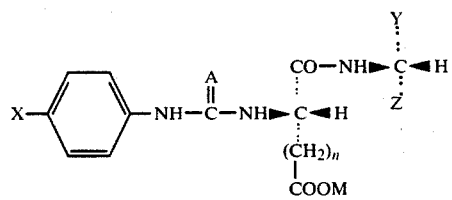

wherein
x is a CN, COOC$_1$-C$_3$ alkyl, COC$_1$-C$_3$ alkyl, CONH-C$_1$-C$_3$ alkyl, SO$_2$C$_1$-C$_3$ alkyl, SOC$_1$-C$_3$ alkyl, SO$_2$NHC$_1$-C$_3$ alkyl, NO$_2$, F or Cl substituent;
n is 0 or 1;
M is a hydrogen atom or an organic or inorganic physiologically acceptable cation;
Y is a COOC$_1$-C$_3$ alkyl, C$_1$-C$_3$ alkyl, CH$_2$OH, CHOHCH$_3$ or CF$_3$ substituent;
Z is a C$_1$-C$_5$ n-alkyl, isobutyl, isopentyl, phenyl, cyclohexyl, benzyl, cyclohexylmethyl, CH$_2$C$_6$H$_4$OH(p), CH$_2$OC$_1$-C$_4$ alkyl, CH$_2$COOC$_1$-C$_4$ alkyl, CH$_2$SC$_1$-C$_4$ alkyl, CH$_2$CH$_2$SCH$_3$, CH$_2$CH$_2$SO$_2$CH$_3$, COOC$_1$-C$_4$ alkyl, COOC$_3$-C$_7$ cycloalkyl, CONHC$_2$-C$_4$ alkyl, CONHC$_3$-C$_7$ cycloalkyl, CONHC$_3$-C$_7$ thiacycloalkyl, or CONHCH$_2$COOCH$_3$ group; and A is an N—CN group.

2. Sweetening agents according to claim 1, wherein:

X is CN, COOCH$_3$, COOC$_2$H$_5$, COCH$_3$, CONHCH$_3$, SO$_2$CH$_3$ or SO$_2$NHCH$_3$;

n is 1;

M is a hydrogen atom or a Na$^+$, K$^+$, NH$_4$$^+$, ½ Ca$^{2+}$ or ½ Mg$^{2+}$ cation;

Y is COOCH$_3$, CH$_3$ or CH$_2$OH; and

Z is a butyl, pentyl, isobutyl, isopentyl, phenyl, cyclohexyl, benzyl, cyclohexylmethyl, propylamide, 2-butylamide, dicyclopropylcarbinylamide or 2,2,4,4-tetramethylthietan-3-ylamide group.

3. Sweetening agents according to claim 2, wherein said agents consist of a compound of formula:

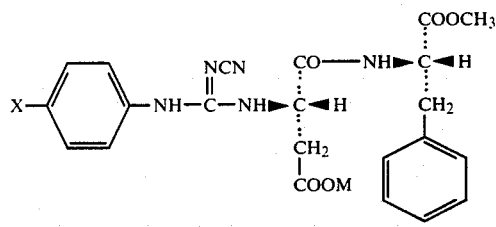

4. Sweetening agents according to claim 2, wherein said agents consist of a compound of formula:

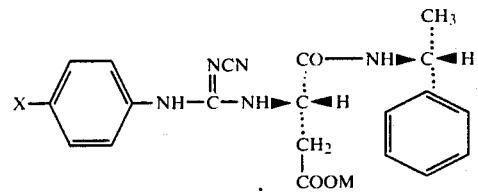

5. Sweetening agents according to claim 2, wherein said agents consist of a compound of the formula:

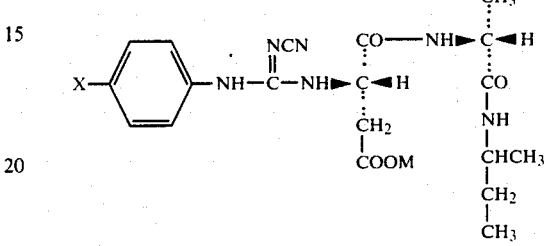

6. A process for sweetening foods, beverages, confectioneries, chewing gums, toilet articles, cosmetics and hygiene products, pharmaceutical and veterinary preparations, said process consisting of adding an adequate quantity of a sweetening agent according to claim 1.

7. Preparations sweetened according to the process of claim 6.

8. Sweetening compositions containing an adequate quantity of a sweetening agent according to claim 1 with a compatible carrier.

9. Sweetening compositions according to claim 8, wherein the compatible carrier is selected from the group including starch, malto-dextrins, cellulose, methylcellulose, carboxymethylcellulose, sodium alginate, pectins, gums, lactose, maltose, glucose, leucine, glycerol, mannitol, sorbitol, and acids such as phosphoric, citric, tartaric, fumaric, benzoic, sorbic and propionic acids, their sodium, potassium and calcium salts, and sodium bicarbonate.

10. Sweetening compositions wherein said compositions contain a sweetening agents according to claim 1, with another sweetening agent, which latter is selected from the group including sucrose, corn syrups, fructose, aspartame, glycyrrhizin, xylitol, acesulfame-K, thaumatin.

* * * * *